United States Patent [19]

Hooven

[11] Patent Number: 5,766,166
[45] Date of Patent: Jun. 16, 1998

[54] BIPOLAR ELECTROSURGICAL SCISSORS

[75] Inventor: Michael D. Hooven, Cincinnati, Ohio

[73] Assignee: Enable Medical Corporation, West Chester, Ohio

[21] Appl. No.: 593,148

[22] Filed: Feb. 1, 1996

Related U.S. Application Data

[63] Continuation-in-part of Ser. No. 399,421, Mar. 7, 1995.

[51] Int. Cl.$^6$ .................................................. A61B 17/39
[52] U.S. Cl. ............................... 606/45; 606/48; 606/51
[58] Field of Search ................... 606/41, 42, 45–52, 606/205; 346/346, 357, 173

[56] References Cited

U.S. PATENT DOCUMENTS

| | | |
|---|---|---|
| Re. 29,088 | 12/1976 | Shaw . |
| 659,409 | 10/1900 | Mosher . |
| 1,586,645 | 6/1926 | Bierman . |
| 1,798,902 | 3/1931 | Raney . |
| 2,433,067 | 12/1947 | Russell . |
| 2,926,232 | 2/1960 | Gard . |
| 3,042,101 | 7/1962 | Spunt . |
| 3,460,539 | 8/1969 | Anhalt . |
| 3,651,811 | 3/1972 | Hildebrandt et al. . |
| 3,685,518 | 8/1972 | Beuerle et al. . |
| 3,730,188 | 5/1973 | Ellman . |
| 3,768,482 | 10/1973 | Shaw . |
| 3,826,263 | 7/1974 | Cage et al. . |
| 3,858,586 | 1/1975 | Lessen . |
| 3,934,115 | 1/1976 | Peterson . |
| 3,970,088 | 7/1976 | Morrison . |
| 3,987,795 | 10/1976 | Morrison . |
| 4,003,380 | 1/1977 | Wien . |
| 4,033,351 | 7/1977 | Hetzel . |
| 4,043,342 | 8/1977 | Morrison, Jr. . |
| 4,092,986 | 6/1978 | Schneiderman . |
| 4,128,099 | 12/1978 | Bauer . |
| 4,161,950 | 7/1979 | Doss et al. . |
| 4,207,896 | 6/1980 | Shaw . |
| 4,228,800 | 10/1980 | Degler, Jr. et al. . |
| 4,232,676 | 11/1980 | Herczog . |
| 4,248,231 | 2/1981 | Herczog et al. . |
| 4,271,838 | 6/1981 | Lasner et al. . |
| 4,353,371 | 10/1982 | Cosman . |
| 4,370,980 | 2/1983 | Lottick . |
| 4,492,231 | 1/1985 | Auth . |
| 4,590,934 | 5/1986 | Malis et al. . |

(List continued on next page.)

FOREIGN PATENT DOCUMENTS

| | | |
|---|---|---|
| 0 572 131 A1 | 1/1993 | European Pat. Off. ........ A61B 17/39 |
| 0717 966 | 6/1996 | European Pat. Off. ........ A61B 17/39 |
| 2 355 521 | 2/1978 | France . |
| 2 647 683 | 12/1990 | France . |
| 342619 | 7/1972 | U.S.S.R. . |
| 575103 | 10/1977 | U.S.S.R. . |
| 1 546 624 | 5/1979 | United Kingdom . |
| 2 037 167 | 7/1980 | United Kingdom . |
| 2 066 104 | 7/1981 | United Kingdom . |
| 2 128 881 | 5/1984 | United Kingdom . |
| 2 133 290 | 7/1984 | United Kingdom . |

OTHER PUBLICATIONS

1979 Brochure entitled, "The Cavitron Bipolar Coagulator," by Cavitron Surgical Systems.
Article entitled, "Combined Biathermy Forceps and Scissors," by D. Lang Stevenson in The Lancet, Oct. 24, 1959.
Article entitled, "Two new laparoscopic instruments: Bipolar sterilizing forceps and uterine manipulator," by Stephen L. Corson, MD, in Association for the Advancement of Medical Instrumentation, Jan.–Feb., 1977 issue.

*Primary Examiner*—Michael Peffley
*Attorney, Agent, or Firm*—Cook, McFarron & Manzo, Ltd.

[57] ABSTRACT

Bipolar electrosurgical scissors are disclosed having a pair of blades joined for relative movement in a scissor-like action between open and closed positions. At least one of the blades comprises a tissue contacting surface and first and second spaced apart electrodes extending along the surface. Current flow between the first and second electrodes promotes hemostasis in tissue contacting the surface. Preferably, each blade of the scissors includes first and second spaced-apart electrodes.

5 Claims, 11 Drawing Sheets

U.S. PATENT DOCUMENTS

| | | |
|---|---|---|
| 4,643,190 | 2/1987 | Heimberger . |
| 4,655,216 | 4/1987 | Tischer . |
| 4,657,017 | 4/1987 | Sorochenko . |
| 4,669,471 | 6/1987 | Hayashi . |
| 4,671,274 | 6/1987 | Sorochenko . |
| 4,674,498 | 6/1987 | Stasz . |
| 4,763,669 | 8/1988 | Jaeger . |
| 4,785,807 | 11/1988 | Blanch . |
| 4,819,633 | 4/1989 | Bauer et al. . |
| 4,848,337 | 7/1989 | Shaw et al. . |
| 4,850,353 | 7/1989 | Stasz et al. . |
| 4,887,612 | 12/1989 | Esser et al. . |
| 4,905,691 | 3/1990 | Rydell . |
| 4,940,468 | 7/1990 | Petillo . |
| 4,944,093 | 7/1990 | Falk . |
| 4,969,885 | 11/1990 | Farin . |
| 4,977,900 | 12/1990 | Fehling et al. . |
| 4,985,030 | 1/1991 | Melzer et al. . |
| 5,007,908 | 4/1991 | Rydell . |
| 5,009,656 | 4/1991 | Reimels . |
| 5,035,696 | 7/1991 | Rydell . |
| 5,047,026 | 9/1991 | Rydell . |
| 5,085,659 | 2/1992 | Rydell . |
| 5,108,391 | 4/1992 | Flachenecker et al. . |
| 5,147,356 | 9/1992 | Bhatta . |
| 5,147,357 | 9/1992 | Rose et al. . |
| 5,250,047 | 10/1993 | Rydell . |
| 5,258,006 | 11/1993 | Rydell et al. . |
| 5,282,799 | 2/1994 | Rydell . |
| 5,308,311 | 5/1994 | Eggers et al. . |
| 5,312,434 | 5/1994 | Crainich . |
| 5,318,564 | 6/1994 | Eggers . |
| 5,324,289 | 6/1994 | Eggers . |
| 5,330,471 | 7/1994 | Eggers . |
| 5,342,359 | 8/1994 | Rydell . |
| 5,342,381 | 8/1994 | Tidemand . |
| 5,352,222 | 10/1994 | Rydell . |
| 5,356,408 | 10/1994 | Rydell . |
| 5,391,166 | 2/1995 | Eggers . |
| 5,403,312 | 4/1995 | Yates et al. . |
| 5,445,638 | 8/1995 | Rydell et al. . |
| 5,456,684 | 10/1995 | Schmidt et al. . |
| 5,462,546 | 10/1995 | Rydell . |
| 5,484,436 | 1/1996 | Eggers et al. . |
| 5,496,312 | 3/1996 | Klicek ................................ 606/51 |
| 5,540,585 | 7/1996 | Parins et al. ........................ 606/51 |

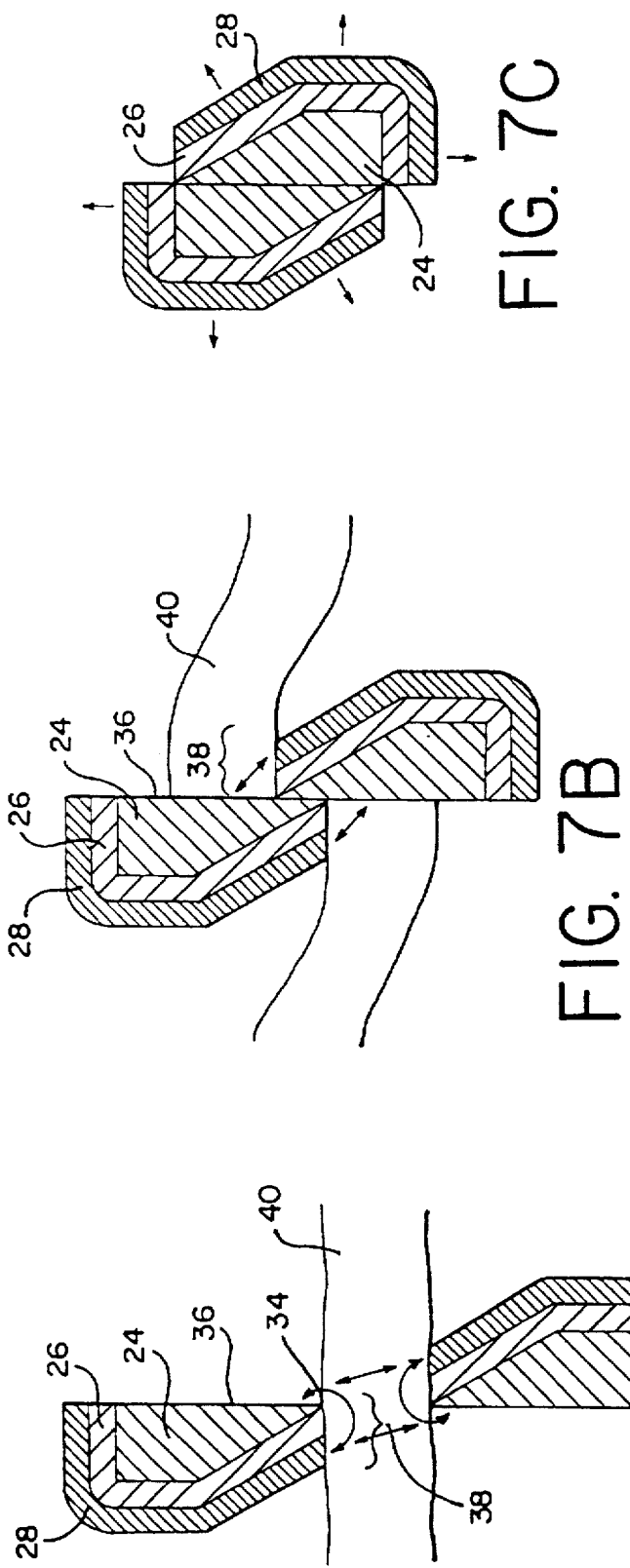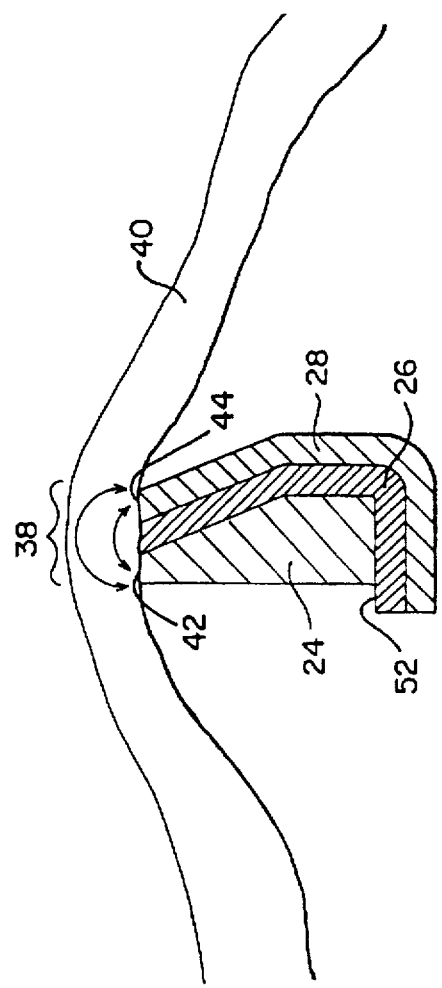

BIPOLAR ELECTROSURGICAL SCISSORS

RELATED APPLICATIONS

This application is a continuation-in-part of application Ser. No. 08/399,421, filed on Mar. 7, 1995.

The present invention relates generally to electrosurgical scissors, and more particularly, to bipolar electrosurgical scissors to assist in hemostasis of tissue as it is cut by the scissors.

BACKGROUND OF THE INVENTION

It is common in many surgical procedures to use surgical scissors for cutting tissue that is vascularized, i.e., contains blood vessels. The resultant bleeding that occurs is not only of concern from the standpoint of blood loss, but the blood may also obscure the surgical field or site. Controlling such bleeding has, in the past, required significant time and attention of the surgeon during many surgical procedures.

In recent years, efforts have been devoted to developing scissors that use radiofrequency ("RF") energy in a manner such that the tissue is heated as it is cut, to promote immediate hemostasis. Early efforts at such electrosurgial scissors used monopolar RF power, where the scissors constituted one electrode, and the patient rested on the other electrode, which was typically in the form of a conductive mat, to complete the circuit. Current flowed generally through the patient between the electrodes due to a voltage applied across the electrodes by an RF power supply.

Monopolar applications, however, had certain drawbacks. Inadvertent contact between the scissors and other tissue could result in unwanted tissue damage. In addition, the flow of current through the body of the patient could take uncertain or unpredictable paths with potential unwanted injury to other tissue. More recently, efforts have been made to develop bipolar electrosurgical scissors to overcome the drawbacks with monopolar scissors. Specifically, efforts have been made to develop scissors in which one blade includes one electrode and the other blade includes the other electrode, so that current flows between the blades as they cut the desired tissue.

Example of recent efforts to develop bipolar scissors are found in U.S. Pat. Nos. 5,324,289 and 5,330,471. These patents disclose bipolar scissors in which one blade of the scissors has one electrode, and the other blade of the scissors has the other electrode, so that current flows between the blades as they come into proximity during cutting. Various embodiments of bipolar scissors are disclosed in these patents, but typically a layer of insulating material is provided on at least one shearing surface of one of the blades, and the hinge pin or fastener which pivotally connects the blades is electrically insulated, so that the electrically active parts of the scissor blades do not contact each other during operation of the instrument. With the construction as shown in these patents, the electrical current flows between the blades at a point just forward of where the shearing surfaces actually touch. The current flow between the blades causes a heating of the tissue and promotes local coagulation and hemostasis during the cutting procedure.

In U.S. Pat. No. 5,352,222, bipolar scissors are shown in which each blade of the scissors is a laminated assembly of a metal shearing surface, a metal blade support and intermediate layer of insulating material. The blade support of one blade acts as one electrode, and the blade support of the other blade acts as the other electrode, so that electrical energy flows between the blade supports as the blades close on the tissue being cut. A short circuit between the shearing surface is prevented by reason of the insulating layer between the metal shearing surface and the blade support. This scissor construction is purported to be more economical to manufacture than the blade structure disclosed in U.S. Pat. Nos. 5,324,289 and 5,330,471. However, because the shearing surface is a separate piece, bonded to the blade support, a particularly high strength and high precision epoxy bonding process is required in the '222 patent so that the shearing surface remains attached to the blade support despite the shearing forces exerted upon it during repeated cutting.

What the above patents have in common, is that each blade forms one of the electrodes attached to a bipolar RF energy source, so that the only current that flows is between the blades as they close. Although the bipolar scissors described in the above-identified patents are believed to be an advance over the earlier monopolar scissors, they typically require the electrically active parts of the blades to be insulated from one another, which tends to complicate the design and materials of the blade actuating mechanism.

Specifically, because only one of the cutting edges of these bipolar scissors acts as an electrode, the blades must be electrically insulated from each other. Further, in current bipolar scissors, at least one of the shearing surfaces is an inactive material. This causes the effectiveness of these bipolar scissors to be highly dependent upon the angle between the cutting plane and the plane of the tissue. More specifically, if current bipolar scissors are angled so that the outer surface of each electrode contacts the tissue, coagulation is optimized. However, if the scissors are angled so that the inner surfaces of each blade contacts the tissue, there will be minimal contact with the outer electrode, which is shielded by the insulator on the shearing surface, adversely affecting coagulation.

A still further problem resulting from the asymmetric construction of the blades of the current bipolar scissors is that hemostasis occurs to a greater extent on the side of the blade opposite the insulating surface. Because only one shearing surface in the scissors is an insulator, asymmetric coagulation results, which can be a significant problem if the physician sees only one side of the scissors.

In addition, the impedance in the current bipolar scissors is high because the current flow goes only along a single path. High impedance systems result in a number of technical and clinical problems. First, bipolar RF generators are typically of low impedance (i.e., the source impedance is typically on the order of 100 ohms). When the impedance of the scissors system is significantly above the source impedance of the generator, the power output is significantly diminished, adversely affecting the ability of the scissors to coagulate blood. In addition, certain sophisticated generators maintain a constant voltage for a given power setting. With the voltage maintained at a constant level, the high impedance of current bipolar scissors sharply reduces the current flow.

The current flow in current bipolar scissors also rapidly dissipates as the blade spacing increases. The result is coagulation typically occurs only at or near the vertex of the blades. Consequently, thick vascular tissue cannot be hemostatically transected because the tissue is not cut at the vertex of the scissors, but at a point significantly ahead of the vertex.

Accordingly, development work continues to provide bipolar scissors which are easy to use, more economical to make, versatile and/or which are effective in promoting hemostasis during cutting of various tissues, particularly including tissues that are highly vascularized and/or thick.

SUMMARY OF INVENTION

In accordance with the present invention, tissue cutting apparatus, such as scissors, may be provided in which each cutting blade itself includes two electrodes for connection to a bipolar RF energy power supply. More specifically, the tissue cutting apparatus of the present invention comprises a pair of blades joined for relative movement in a scissor-like action between open and closed positions. Each of the blades has a tissue contacting surface for contacting the tissue therebetween as the blades close during the cutting action. The tissue contacting surface of at least one and preferably both blades includes first and second spaced-apart electrodes which extend along the tissue contacting surface and are connectable to a voltage source, such as a high frequency bipolar RF power supply, for applying a voltage between the electrodes. As a result, current flows between the first and second electrodes of the blade to promote hemostasis in the tissue as the blade is moved into contact with tissue, such as during the cutting action.

In accordance with other aspects of the present invention, the first electrode of each of the blades may also define a shearing surface and a cutting edge of the blade. As in typical surgical scissors, the shearing surfaces of the blades are in a face-to-face relationship, but in accordance with the preferred aspects of the present invention, the first electrodes of each blade are of like polarity, so that there is no short circuiting between the shearing surfaces of the blades. Because the contacting shearing surfaces are of like polarity, there is no need to insulate the blades from one another, and a less complicated and less expensive scissor construction is required than in the prior patents discussed above. In accordance with this aspect of the present invention, the scissor shaft, which extends between the blades and an actuator handle, may itself be a conductor for connecting the first electrode of each blade to one terminal of a voltage source, and a single insulated conductor extending along the shaft may be used to connect the second electrode of each blade to the other terminal of the voltage source. Further, where the first electrode defines the cutting edge and shearing surface and also serves as the main structural element of each blade, relatively little force is exerted on the second electrode during cutting. As a result, a special high strength or high precision bonding process between the first and second electrodes is unnecessary, and less expensive bonding techniques should suffice.

In the above-described embodiment, the first and second electrodes preferably extend along a tissue contacting edge of the scissors, which is in proximity to the cutting edge. Accordingly, the current flow between the first and second electrodes serves to promote hemostasis in close proximity to the cut line, as the scissors are closed in a cutting action.

In accordance with another feature of the present invention, the first and second electrodes of each blade are located so that current not only flows between the first and second electrodes of each blade, but also between the first electrode of one blade and the second electrode of the other blade as the blades are brought into proximity during cutting. The flow of current between electrodes of different blades and electrodes of the same blade enhances coagulation and hemostasis during the cutting action.

In accordance with another aspect of the present invention, the scissors embodying the present invention may be used to promote coagulation during a blunt dissection or similar procedure, where the opening action of the scissors is used to contact or spread tissue. In this embodiment, each scissor blade has first and second spaced electrodes that extend along the rearward edge of the blades to contact tissue and promote coagulation as the blades are opened to spread or open tissue.

In accordance with yet another aspect of the present invention, the second electrode of each blade may be located in a position relative to its cutting edge such that the second electrodes cooperate to contact and compress the tissue prior to cutting. This elevation of the second electrode relative to the cutting edge acts to promote better sealing of blood vessels due to tissue coaptation during coagulation. The electrodes can be elevated relative to the cutting edge by a number of methods, the two which are shown here include building up the electrode from the cutting edge, or grinding the tissue contacting surface at a 'negative' angle.

These and the many other features of the present invention, are set forth in the following detailed description of the attached drawings.

BRIEF DESCRIPTION OF THE DRAWINGS

FIGS. 7a–7c are vertical cross-sectional views of a further embodiment of scissor blades employing the present invention, showing the positions of the blades as they move from an open position in FIG. 7a in contact with the tissue to be cut, to an intermediate position in FIG. 7b just after the tissue is cut, and to a fully closed position in FIG. 7c.

FIG. 8 is a vertical cross-sectional view of one of the scissor blades of FIG. 6, showing how a single blade may be used to promote hemostasis in tissue.

FIGS. 13a–c and 14a–c depict a further embodiment of the instant invention in which FIGS. 13a and 14a are plan views of scissor blades that together form a pair of blades; FIGS. 13b and 14b are views of the scissor blades of FIGS. 13a and 14a looking down on the tissue contacting surfaces of the blades; and FIGS. 13c and 14c are cross-sectional views of the blades of FIGS. 13a and 14a taken along lines 13c—13c and 14c—14c, respectively.

DETAILED DESCRIPTION OF THE DRAWINGS

Figure 1:
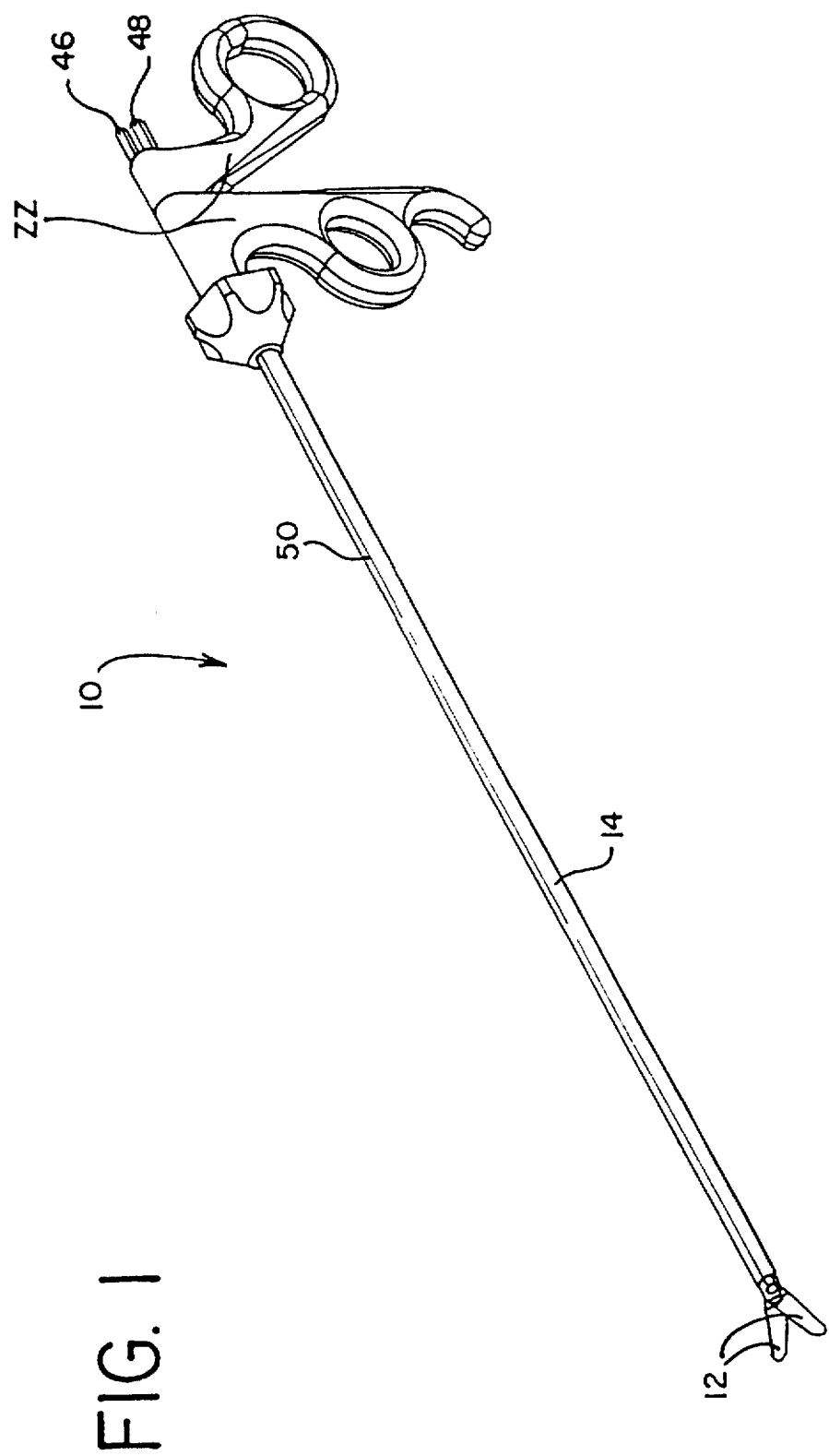
FIG. 1 is a perspective view of electrosurgical scissors embodying the present invention.

Referring to FIG. 1, the present invention is generally embodied in electrosurgical scissors, generally at 10, having a pair of scissor blades 12 joined for pivotal movement between open and closed positions. The present invention is not limited to any particular type or style of surgical scissors, and may be used in essentially any scissors that has a pair of movable blades. The particular scissors 10 shown in FIG. 1 is the type of scissors typically used in so-called minimally invasive surgery, where the scissor blades are inserted into the body cavity of a patient through a small diameter trocar.

Figure 2:
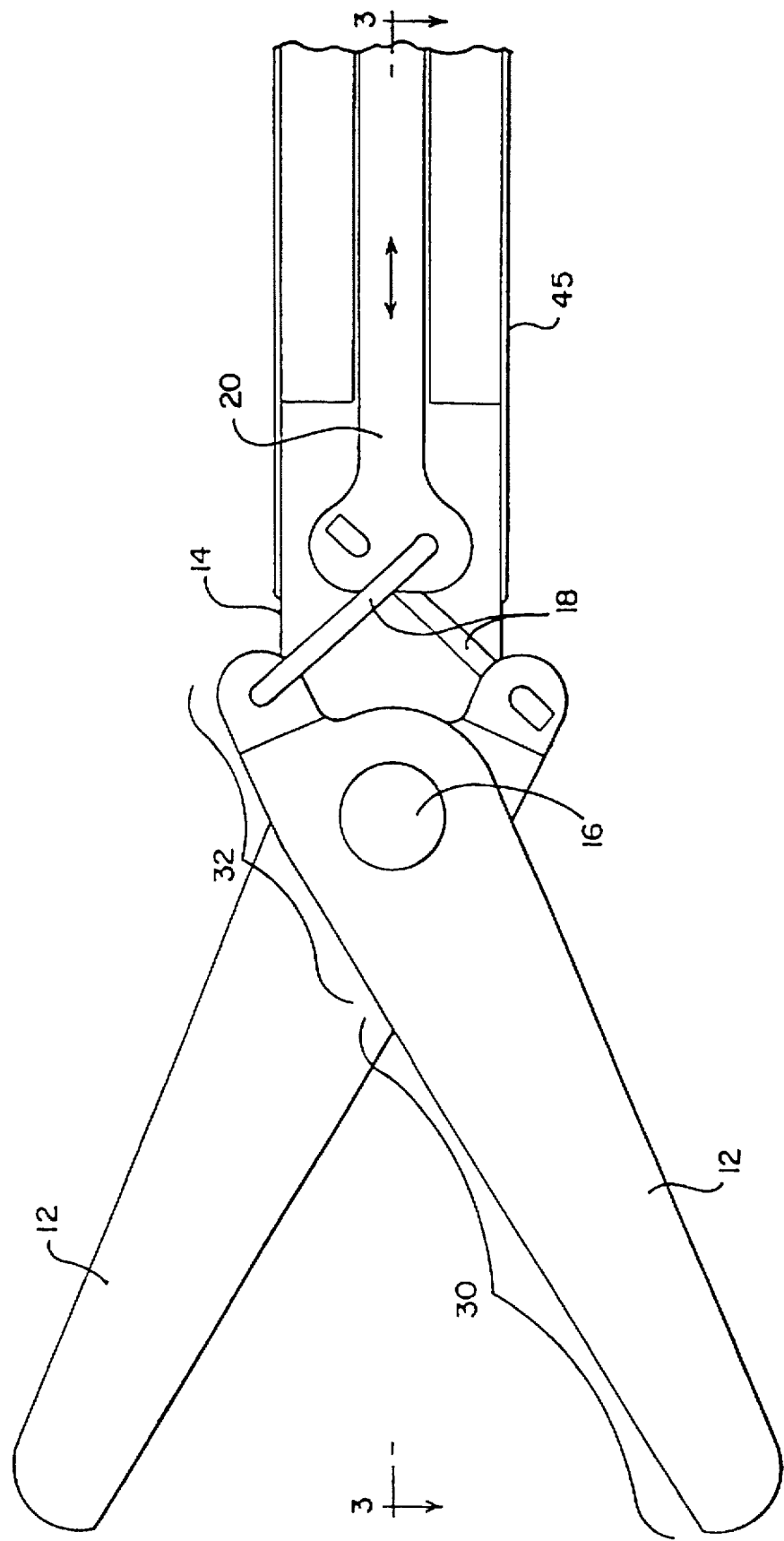
FIG. 2 is an enlarged view of the distal end of the electrosurgical scissors of FIG. 1 in partial cross-section depicting one means for attaching and moving the blades between open and closed positions, with the blades shown in an open position.
Figure 3:
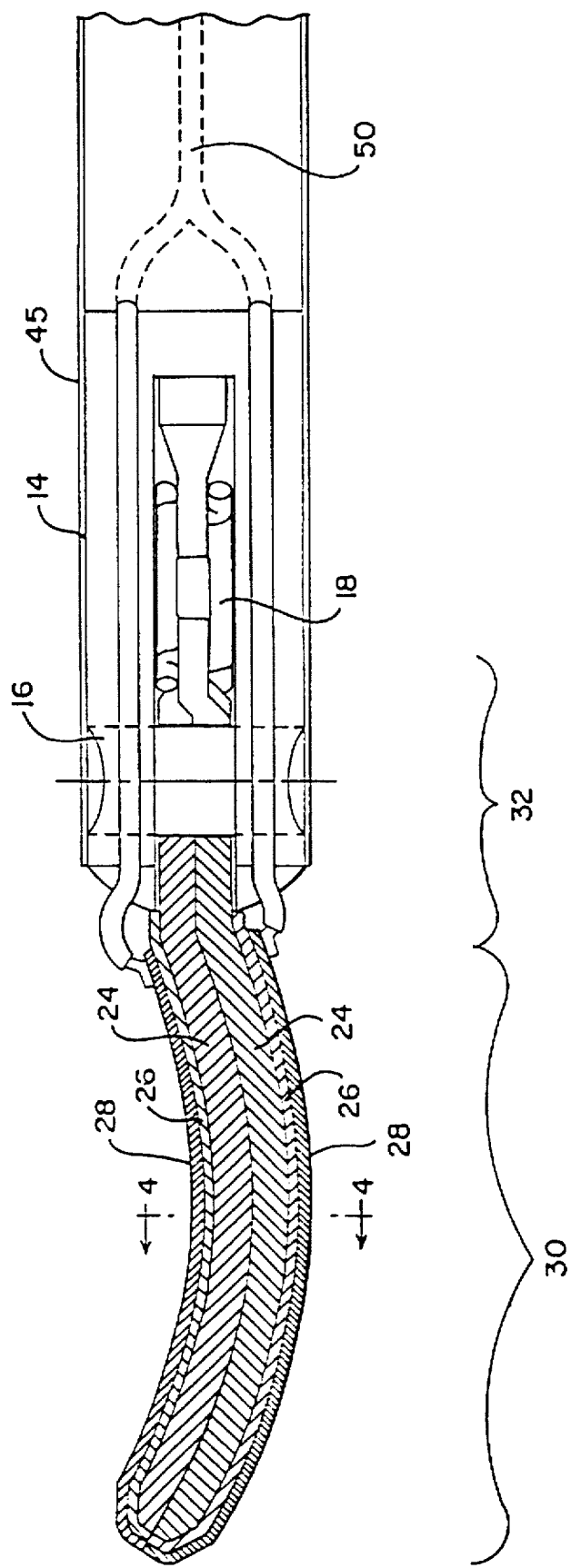
FIG. 3 is a longitudinal cross-sectional view of the distal end of the electrosurgical scissors of FIG. 2, taken along line 3—3 of FIG. 2, with the blades shown in a closed position.

In the scissors 10, the scissor blades are located at the distal end of an elongated tubular shaft 14. As shown in FIGS. 2 and 3, the blades 12 are pivotally attached by pivot pin 16, which also attaches the blades to the distal end of shaft 14. A pair of linkages 18 connect the proximal ends of the blades to an actuator rod 20 that extends through the shaft. Axial movement of the actuator rod, which is controlled by handle 22 (FIG. 1) in a standard and well-known fashion, closes or opens the blades.

Alternatively, the proximal ends of the blades 12 may be slotted and the actuator rod 20 connected to a pin that slides within the slots, so that axial movement of the actuator rod opens and closes the blades. Examples of scissors employing a similar but somewhat more complicated structure than necessary in the present invention are described in U.S. Pat. Nos. 5,330,471 and 5,352,222, which are incorporated by reference herein.

In accordance with the present invention, as shown in FIG. 3, and in FIGS. 4–7, at least one blade, and preferably each blade of the scissors includes an inner conductive blade element 24 which defines a first electrode, an intermediate layer of insulative material 26 and an outer conductive blade element 28 which defines a second electrode. The inner blade element 24 includes a distal curved (or straight if desired) blade segment 30, which extends generally from pivot pin 16, and a proximal mounting segment 32 that is typically received within the end of shaft 14 and receives pivot pin 16 and linkages 18. Referring to FIG. 4a, each blade has a cutting edge 34, a shearing surface 36 and a tissue contact surface or edge 38 that extends along the cutting edge and contacts the tissue 40 as the blades close.

The inner blade element 24 is preferably metal, such as stainless steel, or other suitable material that is of high strength and will hold a sharp cutting edge for repeated use. As best seen in FIGS. 4–7, the inside surface of the inner blade element 24 forms the cutting edge 34 and shearing surface 36 of each blade. A forward surface 42 of the inner blade element extends along the cutting edge and the tissue contact surface for substantially the entire length of the blade segment 30.

Insulative material 26 separates the inner blade element 24 from the outer blade element 28. The insulative material may be made any suitable material that has sufficient resistance to electrically insulate the inner and outer blade elements. Preferably, the insulative material 26 also has sufficient bonding strength for bonding together the inner and outer blade elements. Because the outer blade element 28 does not include the shearing surface or cutting edge, the forces exerted on the outer blade element are limited, and the bond does not have to be as strong, for example, as employed in U.S. Pat. No. 5,352,222. Also, since the insulator does not also comprise a cutting edge as in U.S. Pat. No. 5,330,471, the insulating material does not need to be a hard material such as a ceramic. It is believed that a relatively thin layer or film of insulation, such as the thickness of ordinary electrical tape, will provide sufficient insulation between the inner and outer blade elements. The spacing between inner and outer blade elements at the tissue contact surface is preferably between about 0.002 and 0.050 inches. Ordinary adhesives or materials that are suitable for bonding to metal in medical applications should suffice for bonding the inner and outer blade elements together. Alternatively, epoxy material, such as AF125 by 3M Company, as described in detail in U.S. Pat. No. 5,352,222, may be used to provide the insulative layer. An enamel material, such as Electroscience Labs 9996, may also be used as a high dielectric insulating material.

Outer blade element 28 is preferably a thin metal plate or strip, such as stainless steel or aluminum. Forward edge 44 of outer blade element 28 extends along the tissue contact surface 38, generally parallel to and spaced from the forward surface 42 of the inner blade element 24. As shown in longitudinal cross-section in FIG. 3, the insulating material 26 and outer blade element 28 preferably extend along the entire length of blade segment 30, including around the distal-most end of the blade segment.

The scissors of the present invention are preferably intended for connection to a voltage source, such as to the bipolar terminals of a commercially available bipolar RF energy generator. The bipolar RF generator may be connected to the scissors of the present invention at connectors 46 and 48 located near handle 22. Connector 46 is attached to an insulated conductor 50 that extends through shaft 14 and is connected at the distal end to each of the outer blade elements 28 of each blade. The other connector 48 is in electrical contact with the actuator rod 20 and shaft 14 which, in turn, are in electrical contact with the inner blade elements 24 of each blade via linkage 18 and pivot pin 16, respectively. Accordingly, the inner blade elements of each blade are attached to the same terminal of the voltage source and therefore have the same polarity. A standard insulating material such as plastic shrink tubing acts as a covering 45 along the outside surface of shaft 14, and protects surrounding tissue by preventing inadvertent conduction of electricity to or from the surface of the shaft. Alternatively, the shaft could act as a conductor for the outer blade elements, and the connecting rod could be insulated from the shaft with an insulating coating, and act as a conductor for the inner blade elements.

Figure 4A:
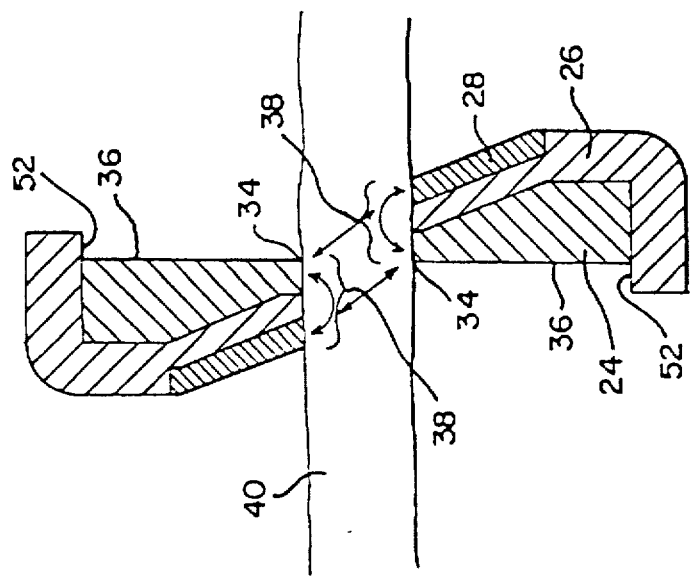
FIGS. 4a–4c are vertical cross-sectional views of one embodiment of scissor blades employing the present invention, taken along line 4—4 of FIG. 3, and showing the positions of the blades as they move from an open position in FIG. 4a in contact with the tissue to be cut, to an intermediate position in FIG. 4b just after the tissue is cut, and to a fully closed position in FIG. 4c.

FIGS. 4–7 show various possible blade configurations, in cross-section, as the blades close on tissue to be severed. Referring first to FIG. 4, FIG. 4a depicts the blades as they are closed and when they first come in contact the tissue 40 to be severed. Each blade has a shearing surface 36 and cutting edge 34. Each blade also includes an inside or forward tissue contacting edge surface 38. The inner blade element 24 forms the cutting edge and shearing surface of each blade. The inner blade also includes the forward edge or surface 42 that extends along the cutting edge for essentially the entire cutting length of the blade. The outer surface and back edge of the inner blade element are covered by insulative material 26. The insulative material 26 also extends beyond the back edge of inner blade element 24 to form an overhanging lip 52 of insulative material. This overhanging lip has a width approximately the same as or slightly greater than the width of the forward edge 42 of the inner blade element.

Outer blade element 28 extends along the tissue contacting edge surface 38 of the blade for substantially the entire length of the blade segment 30, and, as seen in cross-section, overlies only a portion of the outside surface of the inner blade element 24.

As shown by the arrows in FIG. 4a, when the tissue contacting edge or surface 38 of each blade comes into contact with the tissue 40 to be cut, current is believed to flow through the tissue between the inner blade element 24 and the outer blade element 28 of each blade, and as the blades come into proximity with each other, current flows through the tissue between the outer blade element 28 and inner blade element 24 of opposite blades. The current flow at the initial point of contacting the tissue is believed to be substantially between the inner and outer blade elements of the same blade along the tissue contacting edge. As the blades begin to cut the tissue and the distance between the blades decreases, the current flow between opposite electrodes of opposite blades increases.

Figure 4B:
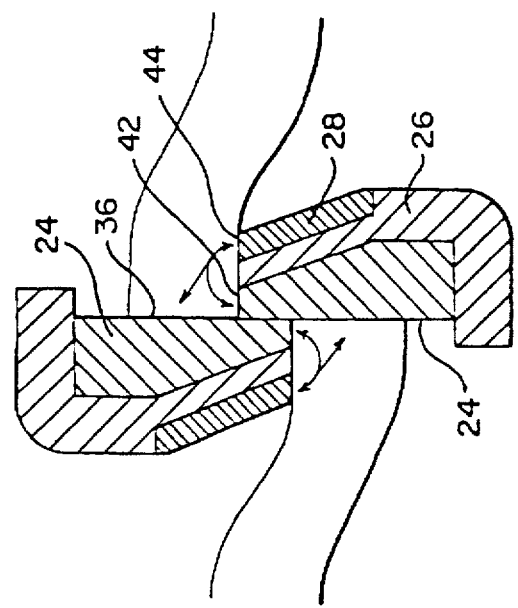

FIG. 4b shows the blades in a position where the tissue has been severed, and the blades are not fully closed. At that position, it is understood that current flows substantially between the inner and outer blade elements of the same blade along the tissue contacting edge or surface 38, and may also flow between the outer blade element 28 and the shearing surface 36 of the inner blade element 24 of the other blade. The extent of current flow through the tissue in this situation may vary depending on the tissue type, position, thickness, and the extent to which the tissue is under tension.

Figure 4C:
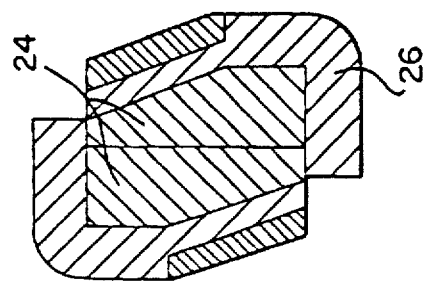

FIG. 4c shows the blades in a fully closed position. At that position, the overhanging lip 52 of insulative material covers the forward edge 42 of the inner blade element 24 of the facing blade, essentially fully enclosing and insulating the inner blade elements 24 from tissue contact, and preventing current flow therethrough.

Figure 5C:
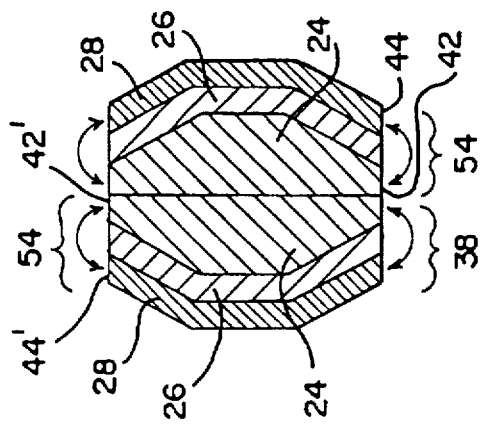
FIGS. 5a–5c are vertical cross-sectional views of another embodiment of scissor blades employing the present invention, showing the positions of the blades as they move from an open position in FIG. 5a in contact with the tissue to be cut, to an intermediate position in FIG. 5b just after the tissue is cut, and to a fully closed position in FIG. 5c.
Figure 5B:
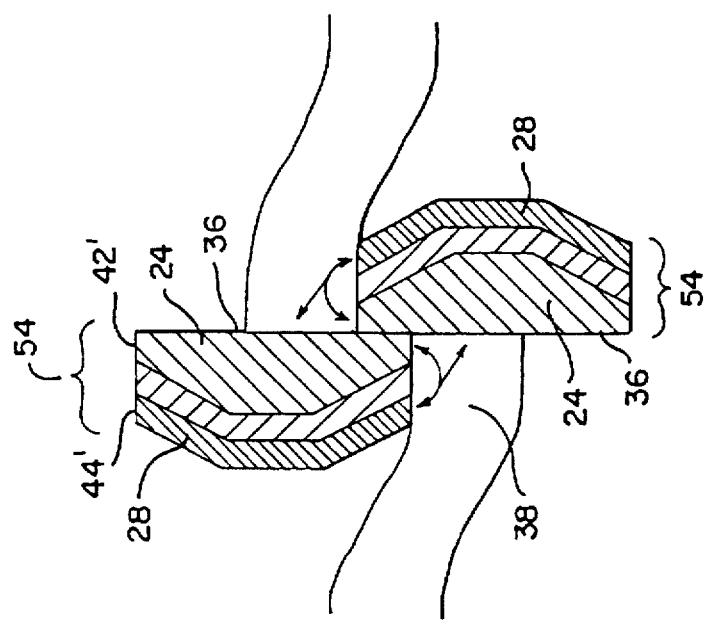
Figure 5A:
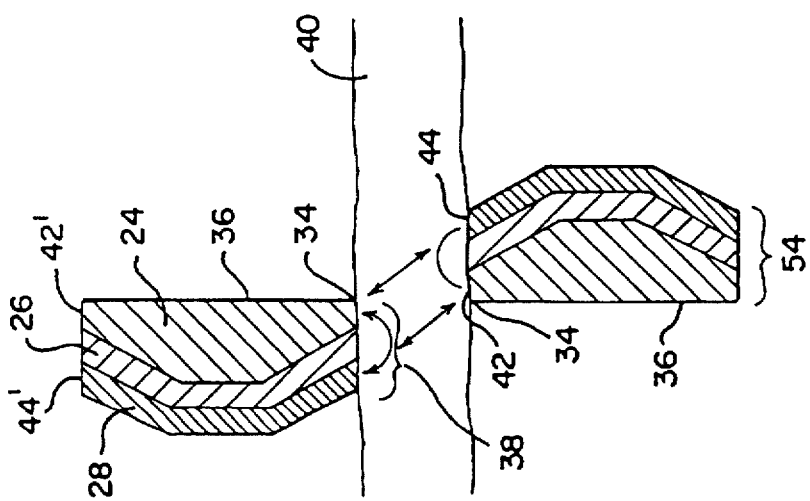

FIGS. 5a–5c show an alternative embodiment of the present invention in which each of the blades similarly has a cutting edge 34, shearing surface 36, and tissue contacting edge or surface 38 for contacting tissue as the blades close. In addition, in this embodiment each of the blades includes an rearward edge or surface 54, which is displaced from or opposite the tissue contacting edge or surface 38, and which may be used for cauterizing tissue in those situations where it is desirable to cauterize tissue with the rearward surfaces of the blades.

More specifically, as shown in FIG. 5a, each blade includes the inner blade element 24, insulative material 26 over only the outside surface of the inner blade element, and outer blade element 28 which fully overlies the outside surface of the inner blade element. With this construction, as the tissue contacting edge of each blade comes into contact with tissue 40 for cutting, current is understood to flow between the surfaces 42 and 44 of the inner and outer elements of the same blade, and between the inner blade surface 42 and the outer blade surface 44 of opposite blades.

As the blades are moved to a closed position, as shown in FIG. 5b, current is believed to flow between the outer blade surface 44 and the inner blade surface 42 of the same blade and between the inner blade element and outer blade element of the opposite blades. When the blades are fully closed, as shown in FIG. 5c, the forward and rearward surfaces 38 and 54 of the inner and outer electrodes of each blade are exposed, and current may continue to flow between the electrodes of each blade, when they are in contact with tissue.

Figure 9C:
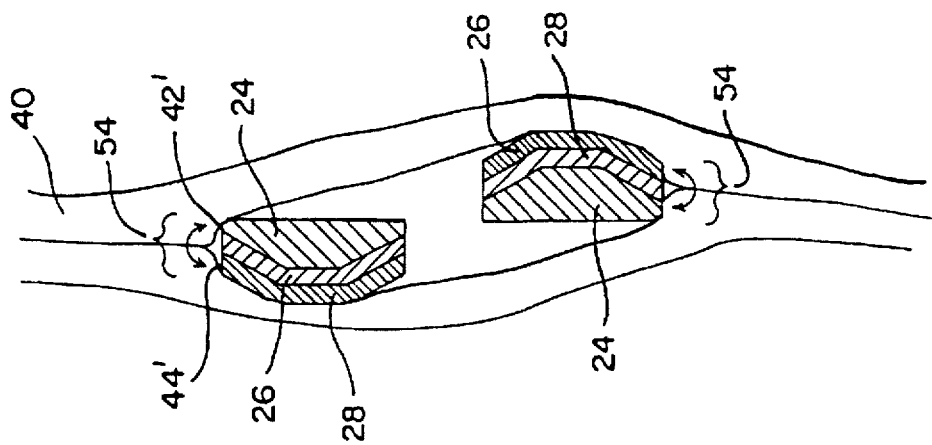
FIGS. 9a–9c are vertical cross-sectional views of the scissor blades of FIG. 5 showing the positions of the blades as they move from a closed position in FIG. 9a, to an intermediate position in FIG. 9b, to an open position in FIG. 9c, during a blunt dissection procedure.
Figure 9B:
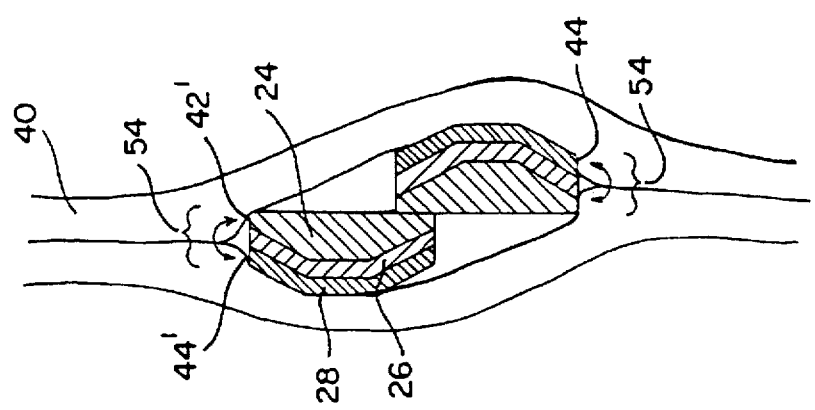
Figure 9A:
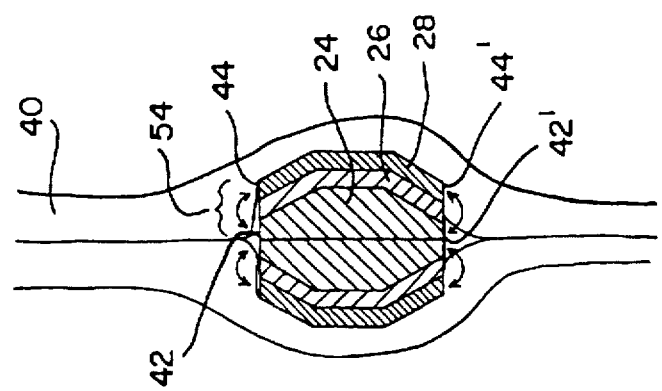

The rearward edge of each blade in FIG. 5 has the same construction as the inside or forward edge of the blade, with tissue contacting surfaces 42' and 44' extending along the rearward surface 54, and therefore may be used for assisting in severing and promoting hemostasis of tissue that is contacted by the outside of the blades in a procedure such as blunt dissection. FIGS. 9a–9c depict use of the scissors of FIG. 5 in a procedure such as a blunt dissection. A blunt dissection as depicted in FIG. 9 is where the scissors are inserted into the tissue in a closed or semiclosed position, and then opened to spread the tissue. Such a spreading action may result in bleeding from blood vessels ruptured during the procedure. In accordance with the present invention, the scissors of FIG. 5 may be used not only for promoting hemostasis during normal cutting but for promoting hemostasis during blunt dissection or the like.

FIG. 9a shows the scissor blades of FIG. 5 inserted into tissue 40 in a closed or near closed position. In this position, current flows through the tissue between surfaces 42 and 44 of the same blade at the inside tissue contacting surface and between surfaces 42' and 44' of the same blade at the rearward tissue contact surfaces. As the blades are moved to an intermediate position, the inside surfaces are no longer in close tissue contact and current flow between the inner and outer blade elements reduces or ceases. Current continues to flow through the tissue in contact with surfaces 42' and 44', promoting hemostasis in the tissue as the scissors spread. This current flow and hemostasis continues as the scissors fully open, as shown in FIG. 9c.

Figure 6C:
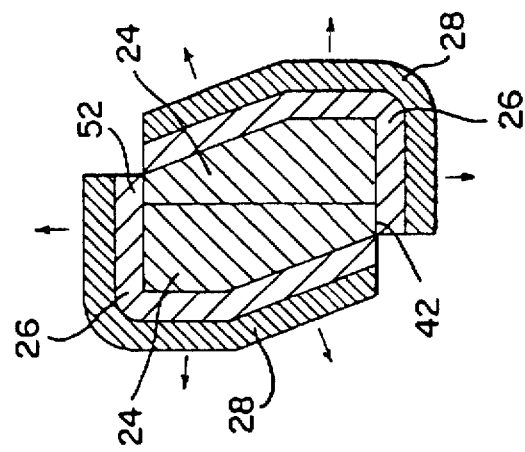
FIGS. 6a–6c are vertical cross-sectional views of a further embodiment of scissor blades employing the present invention, showing the positions of the blades as they move from an open position in FIG. 6a in contact with the tissue to be cut, to an intermediate position in FIG. 6b just after the tissue is cut, and to a fully closed position in FIG. 6c.
Figure 6B:
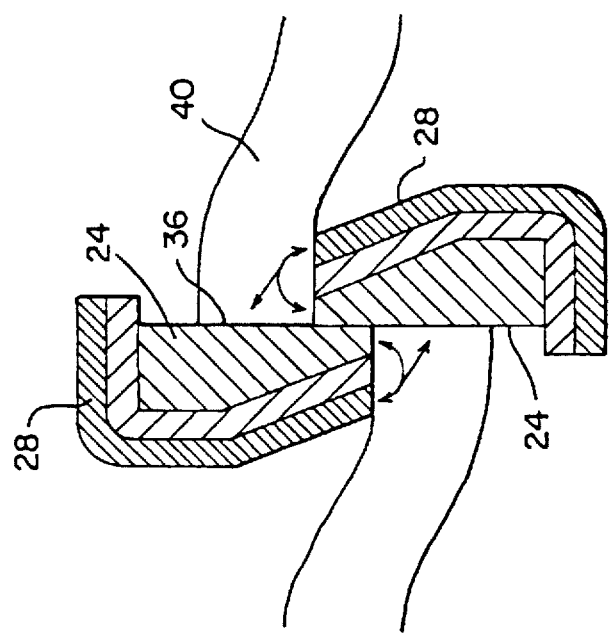
Figure 6A:
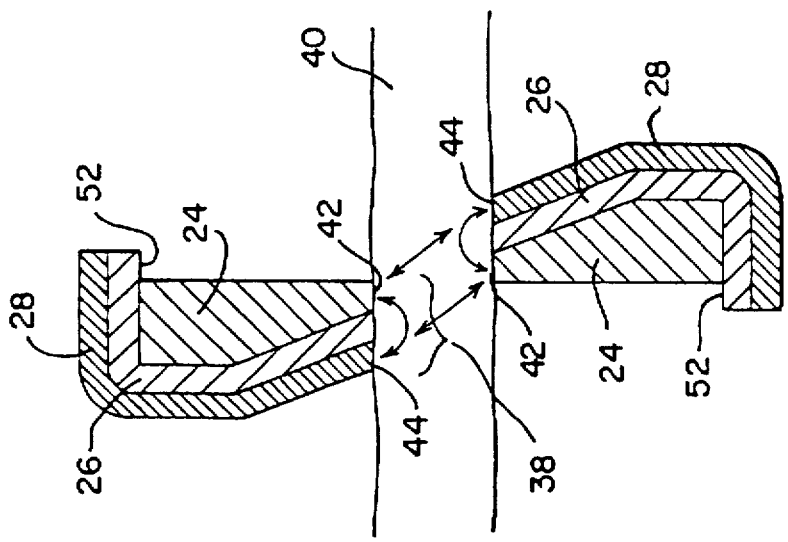

FIG. 6 shows another embodiment of the present invention, in which the inner blade element 24 is of essentially the same shape as that shown in FIG. 4, with the insulative layer 26 covering the same portion of the inner blade element as also shown in FIG. 4. In FIG. 6, however, the outer blade element 28 extends fully around the inner blade element to the same extent that the insulative material 26 extends around the material. The current flow between inner and outer elements of the blades in FIG. 6 is essentially the same as that described for FIG. 4. Also, similarly, when the blades are fully closed the inner blade elements 24 are essentially fully enclosed by the insulative material 26 and current flow between the inner and outer blade elements is effectively prevented. In this configuration, the outer electrode could be used as a monopolar electrode when the scissors are closed.

FIGS. 7a–7c show yet another embodiment of the present invention similar to that of FIG. 6. In this embodiment, however, the inner blade element 24 tapers to a point at the tissue contacting edge or surface. In this embodiment, it is believed that the maximum amount of current flow will occur between the outer blade element of one blade and the inner blade element of the other blade as the blades sever the tissue. It should be noted that the wider the inner blade element surface 42 is, the more current will flow between electrodes (inner and outer elements) of the same blade, and the narrower the surface 42, the more current will flow between electrodes (inner and outer elements) of opposite blades. If the surface 42 width exceeds the typical current path length for bipolar energy (i.e., is greater than about 0.050 inches in width) then most of the current flow will occur between electrodes (inner and outer elements) of the same blade.

Finally, FIG. 8 depicts how the forward or tissue contact surface of a single blade embodying the present invention may be used to promote hemostasis independent of the tissue being severed.

Figure 10:
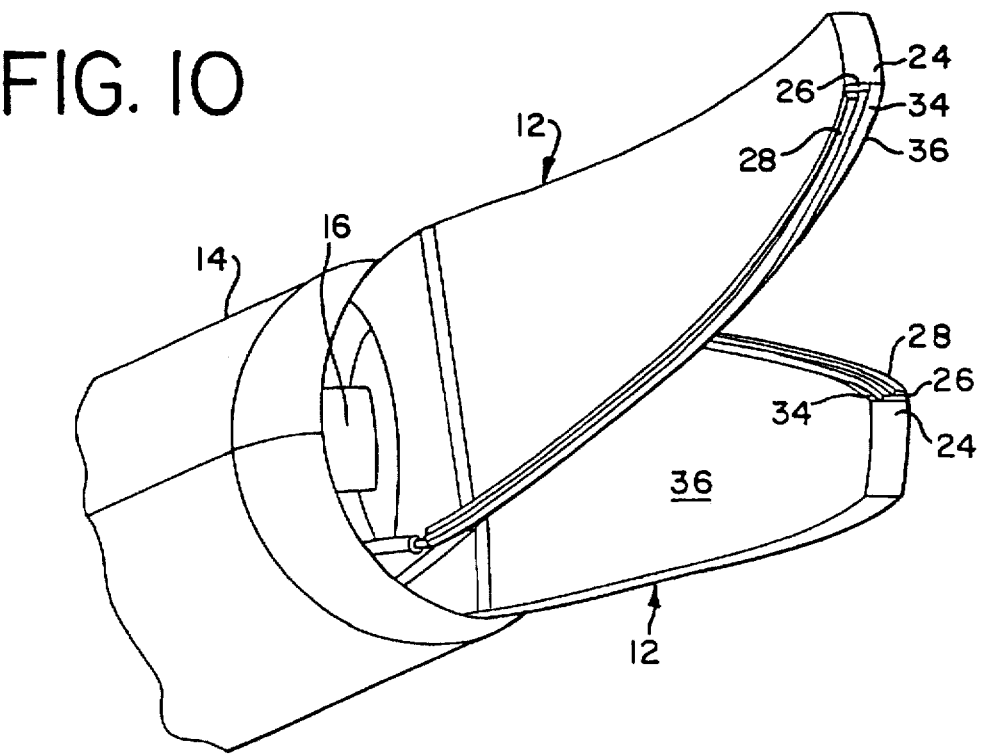
FIG. 10 is a perspective view of the distal end of a further embodiment of scissor blades employing the present invention.
Figure 11:
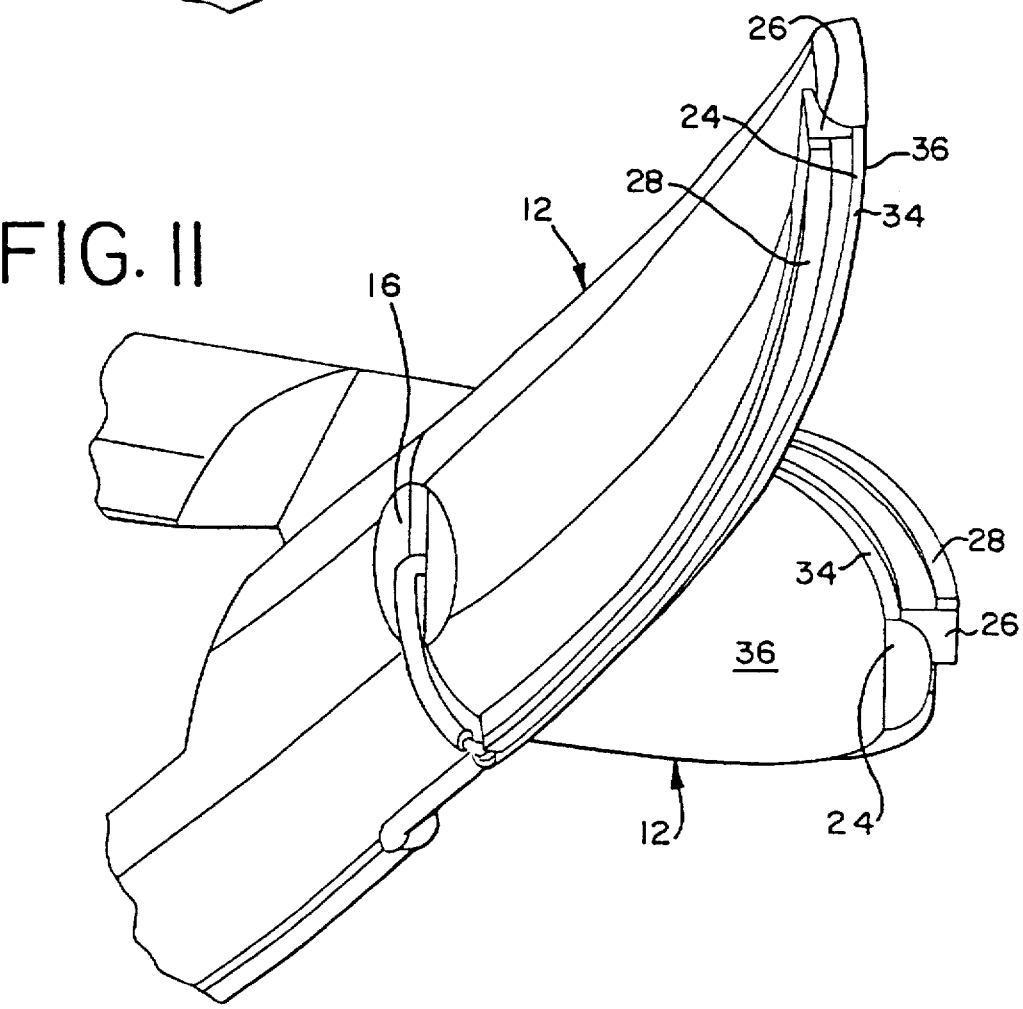
FIG. 11 is a perspective view of the distal end of a still further embodiment of scissor blades employing the present invention.

FIGS. 10 and 11 show two different methods of constructing the electrodes and insulating layer of a blade in accordance with the invention. The components forming the inner and outer electrodes 24 and 28 and the insulative layer 26 are stacked and secured to a substrate that forms the cutting blade 12. The construction of these scissors, in which the surface area of the outer electrode 28 is minimized, reduces the likelihood of any capacitative leakage of current between the inner and outer electrodes of each blade.

Figure 12:
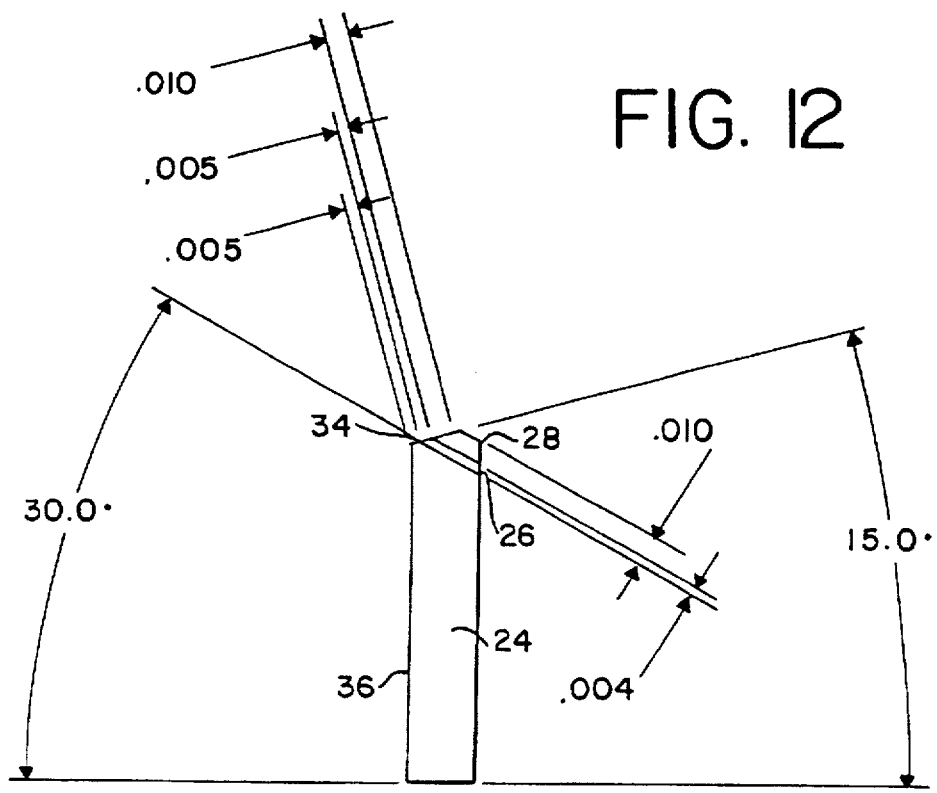
FIG. 12 is a partial cross section of a scissor blade according to the present invention showing the relationship between the angle of the shearing surface to the tissue contacting surface a the width of the electrodes.

As shown in the FIGS. 12 and 13, the blades are not yet sharpened, but are configured to be provided with a "negative" grind angle, that is, the cutting edge of the blade slopes up and away at an obtuse angle with respect to the shearing surface. A "positive" grind angle (i.e., one that forms a cutting edge having an acute angle with respect to the shearing face) would be required if the blades were curved in the opposite direction, and the components forming the electrodes and insulative layer would be placed on the opposite side of the blade (forming a mirror-image to the configuration shown in FIGS. 10 and 11).

Turning to FIG. 12, there is seen an example of a blade according to the present invention having a "negative" grind angle of 15°. A potential method for fabricating such a blade is to use a thermal spray process to deposit an insulator 26, such as ceramic, or the top surface of the inner conductive blade 24. A conductor such as aluminum or stainless steel is then deposited over the ceramic 26 to provide the outer conductive blade element.

As seen in FIG. 12, the top edge of the blade element 24 slopes away from the shearing face 36 at a 30° angle, the thickness of the ceramic layer is 0.004", and the thickness of the outer conductive layer is 0.010". The width of the electrodes and insulating layer along the cutting edge depends upon the depth of the grind. As shown in FIG. 12, the inner conductive blade has a width of 0.005" along its cutting edge; the insulating layer a width of 0.005", and the outer electrode a width of 0.010". Using thicknesses of between 0.004" and 0.020" for each layer, satisfactory electrode/insulator configurations, such as those shown in FIG. 12, can be achieved by grinding the blade edge at a "negative" angle of between approximately 15° and 30°.

Sharpening of the scissors blades is typically achieved by grinding the blades with a flat grinding wheel. When grinding a cutting edge, the exposed surfaces of the inner conductive blade element, the insulation material, and the outer conductive blade element are preferably of uniform width across their entire length after the edge has been sharpened so that a uniform current flow can be maintained along the length of each blade between its inner and outer blade elements. Further, the cutting edge is preferably sharpened at an angle other than perpendicular to the shearing face of the blade in order to ensure good electrode contact with the tissue being cut. If the blades are curved, as shown in FIG. 3, sharpening the cutting edge in the desired manner can be extremely difficult, typically requiring precise adjustment of the height and/or angle of the grinding wheel with respect to the blade. The multiple adjustments of the angle and/or height of the grinding wheel to achieve the desired cutting edge consequently can be an exacting and time-consuming process.

Thus, in keeping with a further aspect of the present invention, the curved blades of the electrosurgical scissors are further configured so that they can be sharpened to a uniform edge, while maintaining a constant height and angle for the grinding wheel with respect to the blade. This is accomplished by providing a cutting edge and tissue contacting surface of one of the blades with a "convex" radius or curve, while providing the cutting edge and tissue contacting surface of the other blade with a "concave" radius or curve.

Figure 13A:
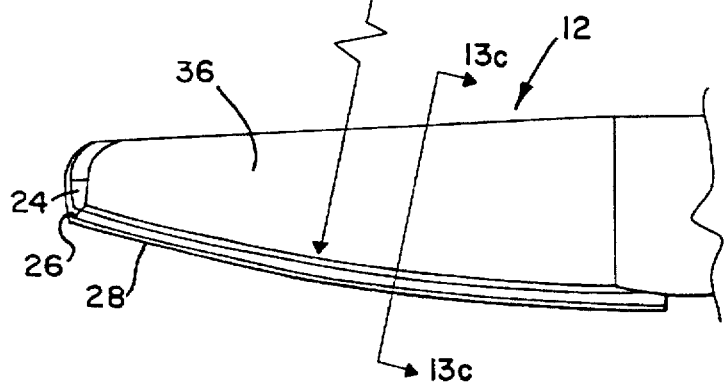
Figure 13B:
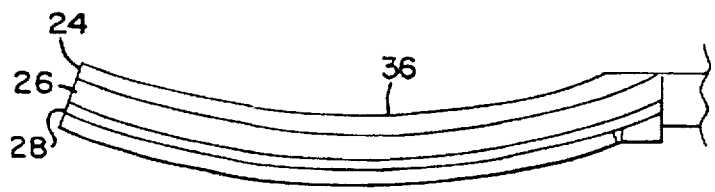
Figure 14A:
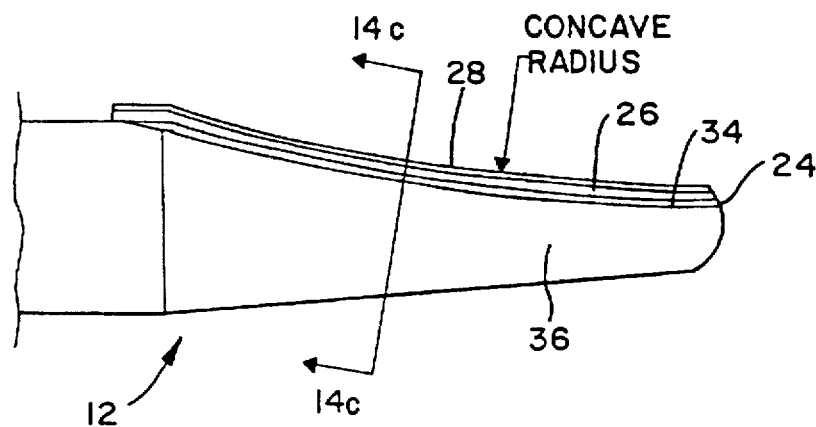

Turning to FIGS. 13a and 14a, there is seen a pair of cooperating scissor blades 12. As described above, each blade 12 includes an inner conductive blade element 24 which has a cutting edge 34 and a shearing surface 36. An insulative material 26 separates the inner conductive blade element 24 from the outer conductive blade element 28. A top view of the cutting edge showing the same elements can be seen in FIGS. 13b and 14b.

Figure 14B:
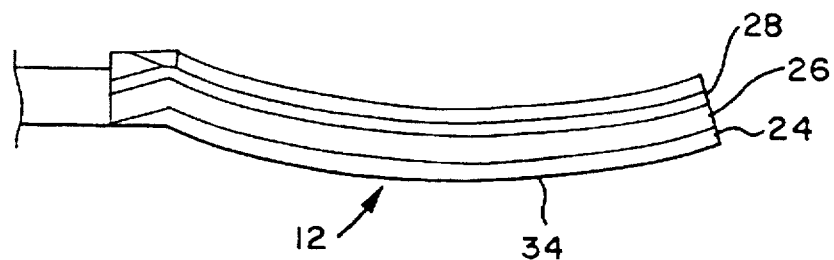

As can be seen in FIGS. 13b and 14b, the shearing surfaces 36 of each blade 12 is formed in a curve substantially perpendicular to the plane of the drawing. In addition, the cutting edge of each blade 12 is also curved. One blade 12 is curved to form a convex arc (labeled "convex radius" in FIG. 13a), while the complementary blade 12 has a cutting edge curved to form a concave arc (labeled "concave radius" in FIG. 14a). The additional radius in the cutting edge results in a cutting edge that can be ground using a flat grinding wheel set at a fixed height above the blade.

Figure 13C:
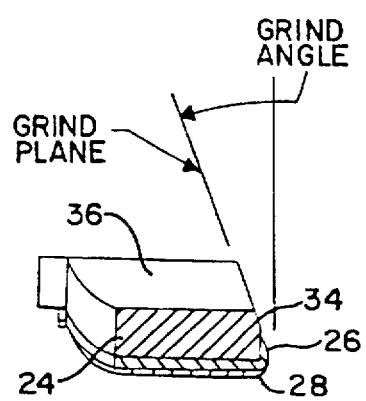
Figure 14C:
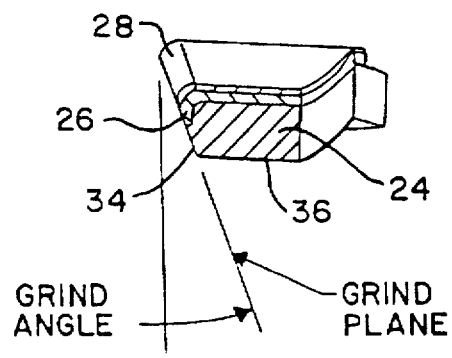

As can be appreciated, the convex and concave radii given to the cutting edges will be a function of the curvature of the blades and the proper radius can be determined either mathematically or empirically. As seen in FIGS. 13c and 14c, the cutting edge can be provided by keeping the flat surface of the grinding wheel in a plane (labeled "grind plane") and securing the blades at an angle thereto (labeled "grind angle"). Consequently, multiple blades can be ground simultaneously in a fixture, instead of individually as before, and wear of the grinding wheel can be compensated for easily by simply adjusting the wheel height above the blade.

Both the "built-up" electrode (FIGS. 10, 11) and the "negative grind" angle (FIGS. 12–14) are methods to achieve a configuration where the tissue contacting surface and electrode are raised relative to the cutting edge. This is advantageous in that during the cutting of tissue, the tissue is first compressed prior to cutting. This 'coaptation' of tissue is a known technique used in sealing blood vessels with bipolar cautery, and may enhance the coagulation and sealing performance of the scissors. Elevation of the electrode also reduces the positional sensitivity of the instrument, since tissue contact with both electrodes occurs even at severe angles.

The invention, as illustrated, is suitable for use in both minimally invasive surgical procedures (e.g., the scissors illustrated in FIGS. 1–3 and 10) or open surgical procedures (e.g., the scissors illustrated in FIG. 11). Such open procedures particularly well suited to the use of the scissors of FIG. 11 include laparotomies, or surgical sections of the abdominal wall. In such procedures, the inventive scissors can be advantageously used to control bleeding. For example, the inventive scissors can be used to cut and cauterize small to moderate-sized vessels in a single motion with activation of the scissors by a foot pedal. Such open scissors can also be used for pinpoint and zone coagulation (where the tips of the scissors are placed on the area to be coagulated), or for "pre-sealing" larger vessels prior to cutting (by placing the tissue and vessels between the blades of the scissors and activating the scissors prior to cutting to coagulate the tissue).

As now can be readily appreciated, many advantages accrue to the present invention over current bipolar scissors. First, the present invention does not require that the scissor blades be electrically insulated from one another. In fact, the blades must be in electrical contact, since the mating faces comprise the same polarity electrode (i.e. both the shearing surfaces and the surfaces of each blade act as electrodes). Because the shearing surfaces conduct RF energy, cauterization occurs directly at the point of each shearing edge as the scissors cut through tissue.

Further, in contrast to current bipolar scissors, current flow takes place between four electrode pairs because each of the blades comprises a pair of bipolar electrodes. The present invention allows two current paths between the blade pair, and allows current flow between the electrode pairs in each blade. Consequently, the impedance between electrode pairs on the same blades is significantly lower than between opposing blades because of the close spacing of the electrodes on each blade.

The unique electrode configuration of the present invention also permits hemostatic transection of both very thin vascular tissue and thick vascular tissue because cauterization occurs along the entire length of each blade as the tissue is being cut, far ahead of the vertex of the blades.

Further, due to the unique electrode configuration of the present invention, the inner and outer electrodes of each blade are positioned so that rotation of the scissors blades always results in contact between at least one outer and inner electrode pair, thus minimizing positional sensitivity and causing coagulation to occur evenly on both sides of the scissors.

Although the several figures depict various alternative constructions for the blades of the present invention, the present invention is not limited to these particular versions, and it is anticipated that other blade configurations may be used embodying the present invention which depart from the particular construction shown in the figures.

I claim:

1. A tissue cutting apparatus comprising:
   first and second blades joined for relative motion in a scissor-like action between an open and a closed position;
   each blade including a first electrode, a layer of insulative material deposited over said first electrode, and a second electrode deposited over said layer of insulative material, said first electrode, said layer of insulative material, and said second electrode being ground at a constant contact angle relative to said blade.

2. A tissue cutting apparatus comprising:
   first and second blades joined for relative motion in a scissor-like action between an open an a closed position;
   each said first and second blade having a cutting edge a shearing face, and a tissue contacting surface, said cutting edge and at least a portion of said tissue contacting surface of each said first and second blade being substantially coplanar and forming an obtuse angle with respect to said shearing face, so that each said tissue contacting surface is elevated with respect to its cutting edge.

3. The tissue cutting apparatus of claim 2 wherein the tissue contacting surface of each blade comprises an electrode.

4. A method of manufacturing a tissue cutting apparatus comprising at least one blade having a tissue contacting surface, said contacting surface including first and second spaced apart electrodes extending along said contacting surface, said method comprising the steps of:
   providing said first electrode;
   depositing a layer of insulative material over said first electrode;
   depositing said second electrode over said insulative material; and
   grinding said contacting surface across said first electrode, said insulative material, and said second electrode at a constant grind angle.

5. The method of manufacturing according to claim 4, wherein said grind angle is less than ninety degrees.

* * * * *

UNITED STATES PATENT AND TRADEMARK OFFICE
CERTIFICATE OF CORRECTION

PATENT NO. : 5,766,166
DATED : June 16, 1998
INVENTOR(S) : Michael D. HOOVEN

It is certified that error appears in the above-identified patent and that said Letters Patent is hereby corrected as shown below:

On the cover page:

Item no. 22, delete --Feb. 1, 1996-- and insert "Feb. 21, 1996."

Signed and Sealed this

Eighth Day of December, 1998

Attest:

BRUCE LEHMAN

Attesting Officer

Commissioner of Patents and Trademarks